United States Patent
Smith et al.

(10) Patent No.: US 6,201,105 B1
(45) Date of Patent: *Mar. 13, 2001

(54) TUMOR NECROSIS FACTOR RECEPTOR POLYPEPTIDES RECOMBINANT P75 (TYPE II)

(76) Inventors: Craig A. Smith, 20405 5th West; Raymond G. Goodwin, 3322 8th Ave. West, both of Seattle, WA (US) 98119; M. Patricia Beckmann, 15875 Nesika Bay Rd., Poulsbo, WA (US) 98370

(*) Notice: Subject to any disclaimer, the term of this patent is extended or adjusted under 35 U.S.C. 154(b) by 0 days.

This patent is subject to a terminal disclaimer.

(21) Appl. No.: 09/233,461

(22) Filed: Jan. 20, 1999

Related U.S. Application Data

(60) Continuation of application No. 08/953,268, filed on Oct. 17, 1997, which is a division of application No. 08/555,629, filed on Nov. 9, 1995, now abandoned, which is a division of application No. 08/468,453, filed on Jun. 6, 1995, now abandoned, which is a continuation of application No. 08/038,765, filed on Mar. 19, 1993, now abandoned, which is a division of application No. 07/523,635, filed on May 10, 1990, now Pat. No. 5,395,760, which is a continuation-in-part of application No. 07/421,417, filed on Oct. 13, 1989, now abandoned, which is a continuation-in-part of application No. 07/405,370, filed on Sep. 11, 1989, now abandoned, which is a continuation-in-part of application No. 07/403,241, filed on Sep. 5, 1989, now abandoned.

(51) Int. Cl.[7] .................... C07K 14/715; C12N 15/12
(52) U.S. Cl. ............................. 530/350; 435/69.1
(58) Field of Search .................. 530/350; 435/69.1

(56) References Cited

U.S. PATENT DOCUMENTS

| | | |
|---|---|---|
| 4,935,233 | 6/1990 | Bell . |
| 5,116,964 | 5/1992 | Capon . |
| 5,155,027 | 10/1992 | Sledziewski . |
| 5,395,760 | 3/1995 | Smith . |
| 5,447,851 | 9/1995 | Beutler . |
| 5,478,925 | 12/1995 | Wallach . |
| 5,512,544 | 4/1996 | Wallach . |
| 5,605,690 | 2/1997 | Jacobs . |
| 5,610,279 | 3/1997 | Brockhaus . |
| 5,695,953 | 12/1997 | Wallach . |
| 5,712,155 | 1/1998 | Smith . |
| 5,945,397 | * 8/1999 | Smith et al. .............. 514/2 |

FOREIGN PATENT DOCUMENTS

| | | |
|---|---|---|
| 325224 | 7/1989 | (EP) . |
| 0394827 | 4/1990 | (EP) . |
| 417563 | 3/1991 | (EP) . |
| 418014 | 3/1991 | (EP) . |
| 464533 | 6/1991 | (EP) . |
| WO 8902922 | 4/1989 | (WO) . |
| WO 9108298 | 6/1991 | (WO) . |

OTHER PUBLICATIONS

Ashkenazi et al, *Proc. Natl. Acad. Sci., USA*, 88:10535–10539 (1991).
Capon et al, *Nature*, 337:525–530 (1989).
Evans et al, *J. Exp. Med.*, 180:2173–2179 (1994).
Imamura et al, *J. Immunol.*, 139:2989–2992 (1987).
Ishikura et al, *Blood*, 73:419–424 (1989).
Jones et al, *Nature*, 338:225–228 (1989).
Langer et al, In: *New Advances on Cytokines*, Eds. Romagnani et al, Raven Press, New York, pp. 349–354 (1992).
Lesslauer et al, *Eur. J. Immunol.*, 21:2883–2886 (1991).
Loetscher et al, *J. Biol. Chem.*, 266:18324–18239 (1991).
Mohler et al, *J. Immunol.*, 151:1548–1561 (1993).
Peppel et al, *J. Cell Biochem. Supp.*, 0(15 Part F):118 (1991).
Peppel et al, *J. Exp. Med.*, 174:1483–1489 (1991).
Rutka et al, *Int. J. Cancer Res.*, 41:573–582 (1988).
Smith et al, *J. Biol. Chem.*, 262:6951–6954 (1987).
Dembic et al, *Cytokine*, 2:231–237 (1990).
Kohno et al, *Proc. Natl. Acad. Sci., USA*, 87:8331–8335 (1990).
Loetscher et al, *Cell*, 61:351–359 (1990).
Nophar et al, *Embo J.*, 9:3269–3278 (1990).

* cited by examiner

*Primary Examiner*—David L. Fitzgerald
(74) *Attorney, Agent, or Firm*—Sughrue, Mion, Zinn, Macpeak & Seas, PLLC

(57) ABSTRACT

Tumor necrosis factor receptor proteins, DNAs and expression vectors encoding TNF receptors, and processes for producing TNF receptors as products of recombinant cell culture, are disclosed.

4 Claims, 10 Drawing Sheets

FIGURE 2A

```
                                                    GCGAGGCAGGCAGCCTGGAGAGAAGGCG                         28

CTGGGCTGCGAGGGCGCGAGGGCGCGAGGGCAGGGCAACCGGACCCCGCCCGCATCC                                             87

ATG GCG CCC GTC GCC GTC TGG GCC GCG CTG GCC GTC GGA CTG GAG                                          132
Met Ala Pro Val Ala Val Trp Ala Ala Leu Ala Val Gly Leu Glu                                           -8

CTC TGG GCT GCG GCG CAC GCC TTG CCC GCC CAG GTG GCA TTT ACA                                          177
Leu Trp Ala Ala Ala His Ala Leu Pro Ala Gln Val Ala Phe Thr                                            8

CCC TAC GCC CCG GAG CCC GGG AGC ACA TGC CTC AGA GAA TAC                                              222
Pro Tyr Ala Pro Glu Pro Gly Ser Thr Cys Leu Arg Glu Tyr                                               23

TAT GAC CAG ACA GCT CAG ATG TGC AAA TGC TCG CCG GGC                                                  267
Tyr Asp Gln Thr Ala Gln Met Cys Lys Cys Ser Pro Gly                                                   38

CAA CAT GCA AAA GTC TTC TGT ACC AAG ACC TCG GAC ACC GTG TGT                                          312
Gln His Ala Lys Val Phe Cys Thr Lys Thr Ser Asp Thr Val Cys                                           53

GAC TCC TGT GAG GAC AGC ACA TAC ACC CAG CTC TGG AAC TGG GTT                                          357
Asp Ser Cys Glu Asp Ser Thr Tyr Thr Gln Leu Trp Asn Trp Val                                           68

CCC GAG TGC TTG AGC TGT GGC TCC CGC AGC TCT GAC AGC CAG GTG                                          402
Pro Glu Cys Leu Ser Cys Gly Ser Arg Ser Ser Asp Ser Gln Val                                           83

GAA ACT CAA GCC TGC ACT CGG GAA CAG AAC CGC ATC TGC ACC TGC                                          447
Glu Thr Gln Ala Cys Thr Arg Glu Gln Asn Arg Ile Cys Thr Cys                                           98
```

FIGURE 2B

```
AGG CCC GGC TGG TAC TGC GCG CTG AGC AAG CAG GAG GGG TGC CGG      492
Arg Pro Gly Trp Tyr Cys Ala Leu Ser Lys Gln Glu Gly Cys Arg      113

CTG TGC GCG CCG CTG CGC AAG TGC CGC CCG TTC GGC GTG GCC          537
Leu Cys Ala Pro Leu Arg Lys Cys Arg Pro Gly Phe Gly Val Ala      128

AGA CCA GGA ACT GAA ACA TCA GAC GTG GTG TGC AAG CCC TGT GCC      582
Arg Pro Gly Thr Glu Thr Ser Asp Val Val Cys Lys Pro Cys Ala      143

CCG GGG ACG TTC TCC AAC ACG ACT TCA TCC ACG GAT ATT TGC AGG      627
Pro Gly Thr Phe Ser Asn Thr Thr Ser Ser Thr Asp Ile Cys Arg      158

CCC CAC CAG ATC TGT AAC GTG GTG GCC ATC CCT GGG AAT GCA AGC      672
Pro His Gln Ile Cys Asn Val Val Ala Ile Pro Gly Asn Ala Ser      173

ATG GAT GCA GTC TGC ACG TCC CCC ACC CGG AGT ATG GCC              717
Met Asp Ala Val Cys Thr Ser Pro Thr Arg Ser Met Ala              188

CCA GGG GCA GTA CAC TTA CCC CAG CCA GTG TCC ACA CGA TCC CAA      762
Pro Gly Ala Val His Leu Pro Gln Pro Val Ser Thr Arg Ser Gln      203

CAC ACG CAG CCA ACT CCA GAA CCC AGC ACT GCT CCA AGC ACC TCC      807
His Thr Gln Pro Thr Pro Glu Pro Ser Thr Ala Pro Ser Thr Ser      218

TTC CTG CCA ATG GGC CCC AGC CCC AGC GCT GAA GGG AGC ACT          852
Phe Leu Pro Met Gly Pro Ser Pro Ser Ala Glu Gly Ser Thr          233
```

FIGURE 2C

```
GGC GAC TTC GCT CTT CCA GTT GGA CTG ATT GTG GGT GTG ACA GCC    897
Gly Asp Phe Ala Leu Pro Val Gly Leu Ile Val Gly Val Thr Ala    248
        ↑
TTG GGT CTA CTA ATA ATA GGA GTG GTG AAC TGT GTC ATC ATG ACC    942
Leu Gly Leu Leu Ile Ile Gly Val Val Asn Cys Val Ile Met Thr    263

CAG GTG AAA AAG AAG CCC TTG TGC CTG CAG AGA GAA GCC AAG GTG    987
Gln Val Lys Lys Lys Pro Leu Cys Leu Gln Arg Glu Ala Lys Val    278

CCT CAC TTG CCT GCC GAT AAG GCC CGG GGT ACA CAG GGC CCC GAG    1032
Pro His Leu Pro Ala Asp Lys Ala Arg Gly Thr Gln Gly Pro Glu    293

CAG CAG CAC CTG ATC CTG CTG ACA GCG CCG AGC TCC AGC AGC TCC    1077
Gln Gln His Leu Ile Leu Leu Thr Ala Pro Ser Ser Ser Ser Ser    308

CTG GAG AGC TCG GCC AGT GCC TTG GAC CTG AGA AGG GCG CCC ACT CGG    1122
Leu Glu Ser Ser Ala Ser Ala Leu Asp Leu Arg Arg Ala Pro Thr Arg    323

AAC CAG CCA CAG GCA CCA GGC GTG GAG GCC AGT GGG GCC GGG GAG    1167
Asn Gln Pro Gln Ala Pro Gly Val Glu Ala Ser Gly Ala Gly Glu    338

GCC CGG GCC AGC ACC AGC TCA GAT TCT TCC CCT GGT GGC CAT    1212
Ala Arg Ala Ser Thr Gly Ser Asp Ser Ser Pro Gly Gly His    353

GGG ACC CAG GTC AAT GTC ACC ATC GTG AAC GTC TGT AGC AGC    1257
Gly Thr Gln Val Asn Val Thr Ile Val Asn Val Cys Ser Ser    368

TCT GAC CAC AGC TCA CAG TGC TCC CAA GCC AGC TCC ACA ATG    1302
Ser Asp His Ser Ser Gln Cys Ser Gln Ala Ser Ser Thr Met    383
```

FIGURE 2D

```
GGA GAC ACA GAT TCC AGC CCC TCG GAG TCC CCG AAG GAC GAG CAG       1347
Gly Asp Thr Asp Ser Ser Pro Ser Glu Ser Pro Lys Asp Glu Gln        398

GTC CCC TTC TCC AAG GAG GAA TGT GCC TTT CGG TCA CAG CTG GAG       1392
Val Pro Phe Ser Lys Glu Glu Cys Ala Phe Arg Ser Gln Leu Glu        413

ACG CCA GAG ACC CTG CTG GGG AGC ACC GAA GAG AAG CCC CTG CCC       1437
Thr Pro Glu Thr Leu Leu Gly Ser Thr Glu Glu Lys Pro Leu Pro        428

CTT GGA GTG CCT GAT GCT GGG ATG AAG CCC AGT                       1470
Leu Gly Val Pro Asp Ala Gly Met Lys Pro Ser                        439

TAACCAGGCCGGTGTGTGGGCTGTGTCGTAGCCAAGGTGGGCTGAGCCCTGGCAGGATGAC

CCTGCGAAGGGCCCCTGGTCCCTTCCAGGCCCCACCACTAGGACTCTGAGGCTCTTTCT

GGGCCAAGTTCCTCTAGTGCCCTCCACAGCCGCAGCCCTCCCCTCTGACCTGCAG...
```

FIGURE 3A

```
                                                                           23
AGGCACAAGGGGCGGGAGCCACCGCTGCCCCT ATG GCG CCC GCC CTC TGG                   75
                                 Met Ala Pro Ala Leu Trp                  -16

GTC GCG CTG GTC TTC GAA CTG CAG CTG TGG GCC ACC GGG CAC ACA               120
Val Ala Leu Val Phe Glu Leu Gln Leu Trp Ala Thr Gly His Thr                -1

GTG CCC GCC CAG GTT GTC TTG ACA CCC TAC AAA CCG GAA CCT GGG               165
Val Pro Ala Gln Val Val Leu Thr Pro Tyr Lys Pro Glu Pro Gly                15

TAC GAG TGC CAG ATC TCA CAG GAA TAC TAT GAC AGG AAG GCT CAG               210
Tyr Glu Cys Gln Ile Ser Gln Glu Tyr Tyr Asp Arg Lys Ala Gln                30

ATG TGC TGT GCT AAG TGT CCT GGC CAA TAT GTG AAA CAT TTC                   255
Met Cys Cys Ala Lys Cys Pro Gly Gln Tyr Val Lys His Phe                    45

TGC AAC AAG ACC TCG GAC ACC GTG TGT GCG GAC TGT GAG GCA AGC               300
Cys Asn Lys Thr Ser Asp Thr Val Cys Ala Asp Cys Glu Ala Ser                60

ATG TAT ACC CAG GTC TGG AAC CAG TTT CGT ACA TGT TTG AGC TGC               345
Met Tyr Thr Gln Val Trp Asn Gln Phe Arg Thr Cys Leu Ser Cys                75

AGT TCT TCC TGT ACC ACT GAC GTG CAG ATC GAG GCC TGC ACT                   390
Ser Ser Ser Cys Thr Thr Asp Val Gln Ile Glu Ala Cys Thr                    90

AAA CAG AAC CGA GTG TGT GCT TGC GAA GCT GGC AGG TAC TGC                   435
Lys Gln Asn Arg Val Cys Ala Cys Glu Ala Gly Arg Tyr Cys                   105
```

FIGURE 3B

```
GCC TTG AAA ACC CAT TCT GGC AGC TGT CGA CAG TGC ATG AGG CTG    480
Ala Leu Lys Thr His Ser Gly Ser Cys Arg Gln Cys Met Arg Leu    120

AGC AAG TGC GGC CCT GGC TTC GGA GTG GCC TCA AGA GCC CCA        525
Ser Lys Cys Gly Pro Gly Phe Gly Val Ala Ser Arg Ala Pro        135

AAT GGA AAT GTG CTA TGC AAG GCC TGT GCC CCA GGG ACG TTC TCT    570
Asn Gly Asn Val Leu Cys Lys Ala Cys Ala Pro Gly Thr Phe Ser    150

GAC ACC ACA TCC ACT GAT GTG TGC AGG CCC CAC CGC ATC TGT        615
Asp Thr Thr Ser Thr Asp Val Cys Arg Pro His Arg Ile Cys        165

AGC ATC CTG GCT ATT CCC GGA AAT GCA AGC ACA AGC GAT GCA GTC TGT    660
Ser Ile Leu Ala Ile Pro Gly Asn Ala Ser Thr Ser Asp Ala Val Cys    180

GCG CCC GAG TCC CCA ACT CTA AGT GCC ATC ATC CCA AGG ACA CTC TAC    705
Ala Pro Glu Ser Pro Thr Leu Ser Ala Ile Ile Pro Arg Thr Leu Tyr    195

GTA TCT CAG CCA GAG CCC ACA AGA TCC CAA CTG GAT CAA GAG        750
Val Ser Gln Pro Glu Pro Thr Arg Ser Gln Leu Asp Gln Glu        210

CCA GGG CCC AGC CAA ACT CCA AGC ATC CTT ACA TCG TTG GGT TCA    795
Pro Gly Pro Ser Gln Thr Pro Ser Ile Leu Thr Ser Leu Gly Ser    225

ACC CCC ATT ATT GAA CAA AGT ACC AAG GGT GGC ATC TCT CTT CCA    840
Thr Pro Ile Ile Glu Gln Ser Thr Lys Gly Gly Ile Ser Leu Pro    240

ATT GGT CTG ATT GTT GGA GTG ACA TCA CTG GGT CTG CTG ATG TTA    885
Ile Gly Leu Ile Val Gly Val Thr Ser Leu Gly Leu Leu Met Leu    255
```

FIGURE 3C

```
GGA CTG GTG AAC TGC ATC ATC CTG GTG CAG AGG AAA AAG AAG CCC      930
Gly Leu Val Asn Cys Ile Ile Leu Val Gln Arg Lys Lys Lys Pro      270

TCC TGC CTA CAA AGA GAT GCC AAG GTG CCT CAT GTG CCT GAT GAG      975
Ser Cys Leu Gln Arg Asp Ala Lys Val Pro His Val Pro Asp Glu      285

AAA TCC CAG GAT GCA GTA GGC CTT GAG CAG CAG CAC CTG TTG ACC     1020
Lys Ser Gln Asp Ala Val Gly Leu Glu Gln Gln His Leu Leu Thr      300

ACA GCA CCC AGT TCC AGC AGC TCC CTA GAG AGC CAT CCC TCA GCC AGC 1065
Thr Ala Pro Ser Ser Ser Ser Leu Glu Ser His Pro Ser Ala Ser     315

GCT GGG GAC CGA AGG AGG GCG CCC CCT GGG GGC CAT CCC CAA GCA AGA 1110
Ala Gly Asp Arg Arg Arg Ala Pro Pro Gly Gly His Pro Gln Ala Arg  330

GTC ATG GCG GAG GCC CAA GGG TTT CAG GAG GCC CGT GCC AGC TCC     1155
Val Met Ala Glu Ala Gln Gly Phe Gln Glu Ala Arg Ala Ser Ser     345

AGG ATT TCA GAT TCT TCC CAC GGA AGC CAC CAC GGG ACC CAC GTC AAC 1200
Arg Ile Ser Asp Ser Ser His Gly Ser His His Gly Thr His Val Asn 360

GTC ACC TGC ATC GTG AAC GTC TGT AGC TCT GAC CAC TCT AGT         1245
Val Thr Cys Ile Val Asn Val Cys Ser Ser Asp His Ser Ser         375

CAG TGC TCT TCC CAA GCC AGC ACA GTG CAG GGA GAC CCA GAT GCC     1290
Gln Cys Ser Ser Gln Ala Ser Thr Val Gln Gly Asp Pro Asp Ala     390

AAG CCC TCA GCG TCC CCA AAG GAT GAG CAG GTC CCC TTC TCT CAG     1335
Lys Pro Ser Ala Ser Pro Lys Asp Glu Gln Val Pro Phe Ser Gln     405
```

FIGURE 3D

```
GAG GAG TGT CCG TCT CAG TCC CCG TGT GAG ACT ACA GAG ACA CTG    1380
Glu Glu Cys Pro Ser Gln Ser Pro Cys Glu Thr Thr Glu Thr Leu     420

CAG AGC CAT GAG AAG CCC TTG CCC CTT GGT GTG CCG GAT ATG GGC    1425
Gln Ser His Glu Lys Pro Leu Pro Leu Gly Val Pro Asp Met Gly     435

ATG AAG CCC AGC CAA GCT GGC TGG TTT GAT CAG ATT GCA GTC AAA    1470
Met Lys Pro Ser Gln Ala Gly Trp Phe Asp Gln Ile Ala Val Lys     450

GTG GCC                                                         1476
Val Ala                                                          452

TGACCCCTGACAGGGGTAACACCCTGCAAAGGGACCCCCGAGACCCTGAACCCATGGAAC   1536
TTCATGACTTTTGCTGGATCCATTCCCTTAGTGGCTTCCAGAGCCCCAGTTGCAGGTCA    1596
AGTGAGGGCTGAGACAGCTAGAGTGGTCAAAAACTGCCATGGTGTTTATGGGGCAGTC    1656
CCAGGAAGTTGTTGCCCCAGTATTTTTCCTCTGGATCTCCTGGGCTCTTGCCTGATTCTT   1716
GCTTCTGAGAGGCCCAGCCTGAATGCTGACACTGCAGGGCGGTTCTAAGGAGCTAACATCCTCTTCCATGAATA   1776
GCACAGTCTTCAGCCTGTAGGGCACAGAGCCCCTTCAGTTGTCTAAACTCTTAGGAAGTACCCT   1836
GGTGGCCTGTAGGGCACAGAGCCCCTTCAGTTGTCTAAACTCTTAGGAAGTACCCT       1896
CTCCAAGCCCACCGAAATTCTTTGATGCAAGAATCAGAGGCCCCATCAGGCAGAGTTGC   1956
TCTGTTATAGGATGGTAGGGCTGTAACTCAGTGGTCCAGTGCTTTTAGCATGCCCTGG    2016
GTTTGATCCTCAGCAACATGCAAAACGTAAGTAGACAAAACGTAAGTAGACAGACAGCAGACAGC  2076
CAGCCCCCTGTGTGGTTTGCAGCCTCTGACTTCTGTCCTCTAATGAGCCCTGAATGAGCCCTCCAAGCCACCCTGTCTCTTCCTACCTCA   2136
GGCTGGAGCTCCTCCTGTAGGACTGTAGAGTTCCAGGGACTGTAGAGTTCCCCAAGGCCACCTGTCTCTTCCTACCTCA   2196
GGAATCTCAGGAGGACTCCCTAACTCCCCAACGGCTTGGTAGTTCCCCAAGCACCCCAAC   2256
GCCTGGAGCACTCCCTAACTCCCCAACGGCTTGGTAGTTCCCCAAGCACCCCAAC         2316
GTGCATTGTCCGGGTTAGGCACTGTGAGTTGGAACAGCTCATGACATCGGTTGAAAGGCC   2376
CACCCGAAACAGCTAAGCCAGCTCTTTGCCAAAGGATTCATGCCGGTTTTCTAATCAA    2436
```

FIGURE 3E

```
CCTGCTCCCTAGCATTGCCTGGAAGGAAAAGGGTTCAGGAGACTCCTCAAGAAGCAAGTTC      2496
AGTCTCAGGTGCTGCTTGGATGCCATGCTCACCGATTCCACTGGATATGAACTTGGCAGAGGA    2556
GCCTAGTTGTTGCCATGGAGACTTAAAGAGCTCAGCACTCTGGAATCAAGATACTGGACA       2616
CTTGGGCCGACTTGTTAAGGCTCTGCAGCATCAGACTGTAGAGGGAAGGAACACGTCT         2676
GCCCCCTGGTGGCCCGTCTGGGTGTGGCCCTAGTCCTGTGCTTGTGTGGATCCCTAAAGGTGT    2736
GGAAAGGATGTTCCTGGGTGTGGCCTAGTCCTGTGCTTGTGTGGATCCCTAAAGGTGT         2796
GCTAAGGAGCAATTGCACTGTGTGCTGGACAGAATTCCTGCTTATAAATGCTTTTGTTG        2856
TTGTTTTGTACACTGAGCCCTGGCTGAGCCACCCCATCCCATCCCACCTTTAC              2916
ACGCCACTCTTGCATGAGAGACTCCCACTTGTAGCCTGTGGATGCTGAGGAA               2976
ACACCCAGCCAAGTAGACTCCAGCTGCTTGCCCTATCCTCCTCGGAACGCCCACACCGTGATGTGA 3036
ATTGTGTGTGGGAAGGAGACGGGTTCTGTCATCTCGGAACGCCCACACCGTGATGTGA         3096
ACAATGGCTGTACTAGCTTAGACCAGCTTAGGGCTCTGCATATCACAGGAGGGGAGCAG        3156
GGAACAATTTGAGTGCTGACCTATAACACAGTTCCTAAAGGATCGGCAGTCCAGAATCT        3216
CCTCCTTCAGTGTGTGTGTGTGTGTGTGTGTGGAGGTTCTGGTGTGTGTGTTCCATGTT        3276
TGCATGTATGTGTGCCAGTGTGTGGAGGCCCGAGGTTGGCTTTGGGTGTGTTTGATCA         3336
CTCTCCAGTTACTGAGGCGGGCTCTCATCTGCCTATGGAGGTGCTCAGTTACAGGCAGGCTGCCAT 3396
ACTTGATTCAGGGATCTCTGTCTGCCTATGGAGGTGCTCAGTTACAGGCAGGCTGCCAT        3456
ACCTGCCCGACATTTACATGAATACTAGAGATCTGAATTCTGGTCCTCCACACTTGTATAC      3516
CTGCATTTTATCCACTAAGACATCTCTCCAAGGGCTCCCCCTTCCTATTTAATAAGTTAG       3576
TTTGAACTGGCAAGATGGCTCAGTGGGTAAGGACCTGGCGACAAACCTGATGACCTG          3636
AGTTGGATCCCTGACCATAAGGTAGAAGAGACCTGCACACATCACATTCTTGCAAGTTGTCCTGACCA 3696
CCACCCCATACATGCTTCTGCATATGTGCACACATCACATTCTTGCACACACTCACAT         3756
ACCATAAATGTAATAAATTTTTTAAATAAATTGATTTTATCTTTTAAAAAAAAA             3813
```

TUMOR NECROSIS FACTOR RECEPTOR POLYPEPTIDES RECOMBINANT P75 (TYPE II)

CROSS-REFERENCE TO RELATED APPLICATION

This is a Continuation of application Ser. No. 08/953,268, filed Oct. 17, 1997; which in turn is a Divisional of application Ser. No. 08/555,629, filed Nov. 9, 1995 (now abandoned); which in turn is a Divisional of application Ser. No. 08/468,453, filed Jun. 6, 1995 (now abandoned); which in turn is a Continuation of application Ser. No. 08/038,765, filed Mar. 19, 1993 (now abandoned); which in turn is a Divisional of application Ser. No. 07/523,635, filed May 10, 1990 (now U.S. Pat. No. 5,395,760); which in turn is a Continuation-In-Part of application Ser. No. 07/421,417, filed Oct. 13, 1989 (now abandoned); which in turn in turn in a Continuation-In-Part of application Ser. No. 07/405,370, filed Sep. 11, 1989 (now abandoned); which in turn is a Continuation-In-Part of application Ser. No. 07/403,241, filed Sep. 5, 1989 (now abandoned).

BACKGROUND OF THE INVENTION

The present invention relates to cytokine receptors and more specifically to tumor necrosis factor receptors.

Tumor necrosis factor (TNFα, also known as cachectin) and tumor necrosis factor-β (TNFβ, also known as lymphotoxin) are homologous mammalian endogenous secretory proteins capable of inducing a wide variety of effects on a large number of cell types. The great similarities in the structural and functional characteristics of these two cytokines have resulted in their collective description as "TNF." Complementary cDNA clones encoding TNFα (Pennica et al., Nature 212:724, 1984) and TNFβ (Gray et al. Nature 312:721, 1984) have been isolated, permitting further structural and biological characterization of TNF.

TNF proteins initiate their biological effect on cells by binding to specific TNF receptor (TNF-R) proteins expressed on the plasma membrane of a TNF-responsive cell. TNFα and TNFβ were first shown to bind to a common receptor on the human cervical cell line ME-180 (Aggarwal et al., Nature 318:665, 1985). Estimates of the size of the TNF-R determined by affinity labeling studies ranged from 54 to 175 kDa (Creasey et al, Proc. Natl. Acad. Sci. USA 84:3293, 1987; Stauber et al., J. Biol. Chem. 263:19098, 1988: Hohmann et al., J. Biol. Chem. 264:14927, 1989). Although the relationship between these TNF-Rs of different molecular mass is unclear, Hohmann et al. (J. Biol. Chem. 264:14927, 1989) reported that at least two different cell surface receptors for TNF exist on different cell types. These receptors have an apparent molecular mass of about 80 kDa and about 55–60 kDa, respectively. None of the above publications, however, reported the purification to homogeneity of cell surface TNF receptors.

In addition to cell surface receptors for TNF, soluble proteins from human urine capable of binding TNF have also been identified (Peetre et al., Eur. J. Haematol. 41:414, 1988; Seckinger et al., J. Exp. Med. 167:1511, 1988; Seckinger et al., J. Biol. Chem. 264:11966, 1989; UK Patent Application, Publ. No. 2 218 101 A to Seckinger et al.; Engelmann et al., J. Biol. Chem. 264:11974, 1989). The soluble urinary TNF binding protein disclosed by UK 2 218 101 A has a partial N-terminal amino acid sequence of Asp-Ser-Val-Cys-Pro-, Cys-Pro-, which corresponds to the partial sequence disclosed later by Engelmann et al. (1989). The relationship of the above soluble urinary binding proteins was further elucidated after original parent application (U.S. Ser. No. 403,241) of the present application was filed, when Engelmann et al. reported the identification and purification of a second distinct soluble urinary TNF binding protein having an N-terminal amino acid sequence of Val-Ala-Phe-Thr-Pro- (J. Biol. Chem. 265:1531, 1990). The two urinary proteins disclosed by the UK 2 218 101 A and the Engelmann et al. publications were shown to be immunochemically related to two apparently distinct cell surface proteins by the ability of antiserum against the binding proteins to inhibit TNF binding to certain cells.

More recently, two separate groups reported the molecular cloning and expression of a human 55 kDa TNF-R (Loetscher et al., Cell 61:351, 1990; Schall et al., Cell 61:361, 1990). The TNF-R of both groups has an N-terminal amino acid sequence which corresponds to the partial amino acid sequence of the urinary binding protein disclosed by UK 2 218 101 A, Engelmann et al. (1989) and Engelmann et al. (1990).

In order to elucidate the relationship of the multiple forms of TNF-R and soluble urinary TNF binding proteins, or to study the structural and biological characteristics of TNF-Rs and the role played by TNF-Rs in the responses of various cell populations to TNF or other cytokine stimulation, or to use TNF-Rs effectively in therapy, diagnosis, or assay, purified compositions of TNF-R are needed. Such compositions, however, are obtainable in practical yields only by cloning and expressing genes encoding the receptors using recombinant DNA technology. Efforts to purify the TNF-R molecule for use in biochemical analysis or to clone and express mammalian genes encoding TNF-R, however, have been impeded by lack of a suitable source of receptor protein or mRNA. Prior to the present invention, no cell lines were known to express high levels of TNF-R constitutively and continuously, which precluded purification of receptor for sequencing or construction of genetic libraries for cDNA cloning.

SUMMARY OF THE INVENTION

The present invention provides isolated TNF receptors and DNA sequences encoding mammalian tumor necrosis factor receptors (TNF-R), in particular, human TNF-Rs. Such DNA sequences include (a) cDNa clones having a nucleotide sequence derived from the coding region of a native TNF-R gene; (b) DNA sequences which are capable of hybridization to the cDNA clones of (a) under moderately stringent conditions and which encode biologically active TNF-R molecules; or (c) DNA sequences which are degenerate as a result of the genetic code to the DNA sequences defined in (a) and (b) and which encode biologically active TNF-R molecules. In particular, the present invention provides DNA sequences which encode soluble TNF receptors.

The present invention also provides recombinant expression vectors comprising the DNA sequences defined above, recombinant TNF-R molecules produced using the recombinant expression vectors, and processes for producing the recombinant TNF-R molecules using the expression vectors.

The present invention also provides isolated or purified protein compositions comprising TNF-R, and, in particular, soluble forms of TNF-R.

The present invention also provides compositions for use in therapy, diagnosis, assay of TNF-R, or in raising antibodies to TNF-R, comprising effective quantities of soluble native or recombinant receptor proteins prepared according to the foregoing processes.

Because of the ability of TNF to specifically bind TNF receptors (TNF-Rs), purified THF-R compositions will be useful in diagnostic assays for TNF, as well as in raising antibodies to TNF receptor for use in diagnosis and therapy. In addition, purified TNF receptor compositions may be used directly in therapy to bind or scavenge TNF, thereby providing a means for regulating the immune activities of this cytokine.

These and other aspects of the present invention will become evident upon reference to the following detailed description.

BRIEF DESCRIPTION OF THE DRAWINGS

FIGS. 2A–2D depict the partial cDNa sequence and derived amino acid sequence of the human TNF-R clone 1. Nucleotides are numbered from the beginning of the 5' untranslated region. Amino acids are numbered from the beginning of the signal peptide sequence. The putative signal peptide sequence is represented by the amino acids −22 to −2. The N-terminal leucine of the mature TNF-R protein is underlined at position 1. The predicted transmembrane region from amino acids 236 to 265 is also underlined. The C-termini of various soluble TNF-Rs are marked with an arrow (↑).

FIGS. 3A–3E depict the cDNA sequence and derived amino acid sequence of murine TNF-R clone 11. The putative signal peptide sequence is represented by amino acids −22 to −1. The N-terminal valine of the mature TNF-R protein is underlined at position 1. The predicted transmembrane region from amino acids 234 to 265 is also underlined.

DETAILED DESCRIPTION OF THE INVENTION

Definitions

Figure 1:
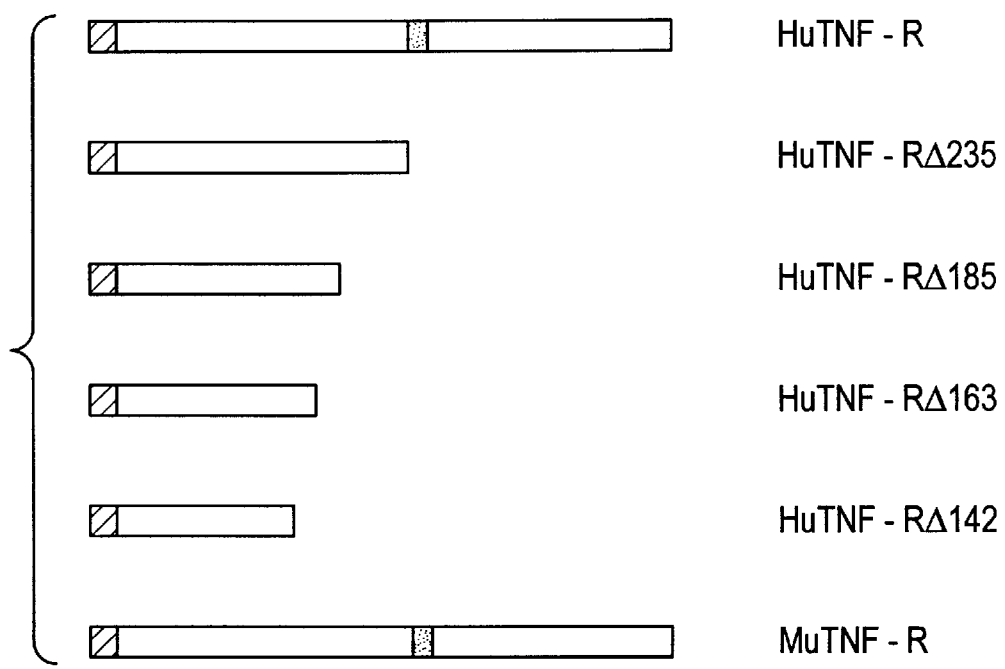
FIG. 1 is a schematic representation of the coding region of various cDNAs encoding human and murine TNF-Rs. The leader sequence is hatched and the transmembrane region is solid.

As used herein, the terms "TNF receptor" and "TNF-R" refer to proteins having amino acid sequences which are substantially similar to the native mammalian TNF receptor amino acid sequences, and which are biologically active, as defined below, in that they are capable of binding TNF molecules or transducing a biological signal initiated by a TNF molecule binding to a cell, or cross-reacting with anti-TNF-R antibodies raised against TNF-R from natural (i.e., nonrecombinant) sources. The mature full-length human TNF-R is a glycoprotein having a molecular weight of about 80 kilodaltons (kDa). As used throughout the specification, the term "mature" means a protein expressed in a form lacking a leader sequence as may be present in full-length transcripts of a native gene. Experiments using COS cells transfected with a cDNA encoding full-length human TNF-R showed that TNF-R bound $^{125}$I-TNFα with an apparent $K_a$ of about $5 \times 10^9$ M$^{-1}$, and that TNF-R bound $^{125}$I-TNFβ with an apparent $K_a$ of about $2 \times 10^9$ M$^{-1}$. The terms "TNF receptor" or "TNF-F" include, but are not limited to, analogs or subunits of native proteins having at least 20 amino acids and which exhibit at least some biological activity in common with TNF-R, for example, soluble TNF-R constructs which are devoid of a transmembrane region (and are secreted from the cell) but retain the ability to bind TNF. Various bioequivalent protein and amino acid analogs are described in detail below.

The nomenclature for TNF-R analogs as used herein follows the conventional of naming the protein (e.g., TNF-R) preceded by either hu (for human) or mu (for murine) and followed by a Δ (to designate a deletion) and the number of the C-terminal amino acid. For example, huTNF-RΔ235 refers to human TNF-R having Asp$^{235}$ as the C-terminal amino acid (i.e., a polypeptide having the sequence of amino acids 1–235 of FIGS. 2A–2C). In the absence of any human or murine species designation, TNF-R refers generically to mammalian TNF-R. Similarly, in the absence of any specific designation for deletion mutants, the term TNF-R means all forms of TNF-R, including mutants and analogs which possess TNF-R biological activity.

"Soluble TNF-R" or "sTNF-R" as used in the context of the present invention refer to proteins, or substantially equivalent analogs, having an amino acid sequence corresponding to all or part of the extracellular region of a native TNF-R, for example, huTNF-RΔ235, huTNF-RΔ185 and huTNF-RΔ163, or amino acid sequences substantially similar to the sequences of amino acids 1–163, amino acids 1–185, or amino acids 1–235 of FIGS. 2A–2C, and which are biologically active in the they bind to TNF ligand. Equivalent soluble TNF-Rs include polypeptides which vary from these sequences by one or more substitutions, deletions, or additions, and which retain the ability to bind TNF or inhibit TNF signal transduction activity via cell surface bound TNF receptor proteins, for example huTNF-RΔx, wherein x is selected from the group consisting of any one of amino acids 163–235 of FIGS. 2B–2C. Analogous deletions may be made to muTNF-R. Inhibition of TNF signal transduction activity can be determined by transfecting cells with recombinant TNF-R DNAs to obtain recombinant receptor expression. The cells are then contacted with TNF and the resulting metabolic effects examined. If an effect results which is attributable to the action of the ligand, then the recombinant receptor has signal transduction activity. Exemplary procedures for determining whether a polypeptide has signal transduction activity are disclosed by Idzerda et al., *J. Exp. Med.* 171:861 (1990); Curtis et al., *Proc. Natl. Acad. Sci. USA* 86:3045 (1989); Prywes et al., *EMBO J.* 5:2179 (1986) and Chou et al., *J. Biol. Chem.* 262:1842 (1987). Alternatively, primary cells or cell lines which express an endogenous TNF receptor and have a detectable biological response to TNF could also be utilized.

The term "isolated" or "purified", as used in the context of this specification to define the purity of TNF-R protein or protein compositions, means that the protein or protein composition is substantially free of other proteins of natural or endogenous origin and contains less than about 1% by mass of protein contaminants residual of production processes. Such compositions, however, can contain other proteins added as stabilizers, carriers, excipients or co-therapeutics. TNF-R is isolated if it is detectable as a single protein band in a polyacrylamide gel by silver staining.

The term "substantially similar," when used to define either amino acid or nucleic acid sequences, means that a particular subject sequence, for example, a mutant sequence, varies from a reference sequence by one or more substitutions, deletions, or additions, the net effect of which is to retain biological activity of the TNF-R protein as may be determined, for example, in one of the TNF-R binding assays set forth in Example 1 below. Alternatively, nucleic acid subunits and analogs are "substantially similar" to the specific DNA sequences disclosed herein if: (a) the DNA sequence is derived from the coding region of a native mammalian TNF-R gene; (b) the DNA sequence is capable of hybridization to DNA sequences of (a) under moderately stringent conditions (50° C., 2× SCC) and which encode biologically active TNF-R molecules; or DNA sequences which are degenerate as a result of the genetic code to the DNA sequences defined in (a) or (b) and which encode biologically active TNF-R molecules.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli*, will be free of glycan. Protein expressed in yeast may have a glycosylation pattern different from that expressed in mammalian cells.

"Biologically active," as used throughout the specification as a characteristic of TNF receptors, means that a particular molecule shares sufficient amino acid sequence similarity with the embodiments of the present invention disclosed herein to be capable of binding detectable quantities of TNF, transmitting a TNF stimulus to a cell, for example, as a component of a hybrid receptor construct, or cross-reacting with anti-TNF-R antibodies raised against TNF-R from natural (i.e., nonrecombinant) sources. Preferably, biologically active TNF receptors within the scope of the present invention are capable of binding greater than 0.1 nmoles TNF per nmole receptor, and most preferably, greater than 0.5 nmole TNF per nmole receptor in standard binding assays (see below).

"Isolated DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used as a source of coding sequences. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided by this invention can be assembled from cDNA fragments and short oligonucleotide linkers, or from a series of oligonucleotides, to provide a synthetic gene which is capable of being expressed in a recombinant transcriptional unit.

Isolation of cDNAs Encoding TNF-R

The coding sequence of TNF-F is obtained by isolating a complementary DNA (cDNA) sequence encoding TNF-R from a recombinant cDNA or genomic DNA library. A cDNA library is preferably constructed by obtaining polyadenylated mRNA from a particular cell line which expresses a mammalian TNF-R, for example, the human fibroblast cell lines WI-26 VA4 (ATCC CCL 95.1) and using the mRNA as a template for synthesizing double stranded cDNA. The double stranded cDNA is then packaged into a recombinant vector, which is introduced into an appropriate *E. coli* strain and propagated. Murine or other mammalian cell lines which express TNF-R may also be used. TNF-R sequences contained in the cDNA library can be readily identified by screening the library with an appropriate nucleic acid probe which is capable of hybridizing with TNF-R cDNA. Alternatively, DNAs encoding TNF-R proteins can be assembled by ligation of synthetic oligonucleotide subunits corresponding to all or part of the sequence of FIGS. 2A–2D or 3A–3E to provide a complete coding sequence.

The human TNF receptor cDNAs of the present invention were isolated by the method of direct expression cloning. A cDNA library was constructed by first isolating cytoplasmic mRNA from the human fibroblast cell lines WI-26 VA4. Polyadenylated RNA was isolated and used to prepare double-stranded cDNA. Purified cDNA fragments were then ligated into pCAV/NOT vector DNA which uses regulatory sequences derived from pDC201 (a derivative of pMLSV, previously described by Cosman et al., *Nature* 312:768: 1984), SV40 and cytomegalovirus DNA, described in detail below in Example 2. pCAV/NOT has been deposited with the American Type Culture Collection under accession No. ACTT 68014. The pCAV/NOT vectors containing the W126-VA4 cDNA fragments were transformed into *E. coli* strain DH5α. Transformants were plated to provide approximately 800 colonies per plate. The resulting colonies were harvested and each pool used to prepare plasmid DNA for transfection into COS-7 cells essentially as described by Cosman et al. (*Nature* 312:768, 1984) and Luthman et al. (*Nucl. Acid Res.* 11:1295, 1983). Transformants expressing biologically active cell surface TNF receptors were identified by screening for their ability to bind $^{125}$I-TNF. In this screening approach, transfected COS-7 cells were incubated with medium containing $^{125}$I-TNF, the cells washed to remove unbound labeled TNF, and the cell monolayers contacted with X-ray film to detect concentrations of TNF binding, as disclosed by Sims et al., *Science* 241:585 (1988). Transfectants detected in this manner appear as dark foci against a relatively light background.

Using this approach, approximately 240,000 cDNAs were screened in pools of approximately 800 cDNAs until assay of one transfectant pool indicated positive foci for TNF binding. A frozen stock of bacteria from this positive pool was grown in culture and plated to provide individual colonies, which were selected until a single clone (clone 1) was identified which was capable of directing synthesis of a surface protein with detectable TNF binding activity. The sequence of cDNA clone 1 by the above method is depicted in FIGS. 2A–2D.

Additional cDNA clones can be isolated from cDNa libraries of other mammalian species by cross-species hybridization. For use in hybridization, DNA encoding TNF-R may by covalently labeled with a detectable substance such as a fluorescent group, a radioactive atom or a chemiluminescent group by methods well known to those skilled in the art. Such probes could also be used for in vitro diagnosis of particular conditions.

Like most mammalian genes, mammalian TNF receptors are presumably encoded by multi-exon genes. Alternative mRNA constructs which can be attributed to different mRNA splicing events following transcription, and which share large regions of identity or similarity with the cDNAs claimed herein, are considered to be within the scope of the present invention.

Other mammalian TNF-R cDNAs are isolated by using an appropriate human TNF-R DNA sequence as a probe for screening a particular mammalian cDNA library by cross-species hybridization.

Proteins and Analogs

The present invention provides isolated recombinant mammalian TNF-R polypeptides. Isolated TNF-R polypeptides of this invention are substantially free of other contaminating materials of natural or endogenous origin and contain less than about 1% by mass of protein contaminants residual of production processes. The native human TNF-R molecules are recovered from cell lysates at glycoproteins having an apparent molecular weight by SDS-PAGE of about 80 kilodaltons (kDa). The TNF-R polypeptides of this invention are optionally without associated native-pattern glycosylation.

Mammalian TNF-R of the present invention includes, by way of example, primate, human, murine, canine, feline, bovine, ovine, equine and porcine TNF-R. Mammalian TNF-Rs can be obtained by cross species hybridization, using a single stranded cDNA derived from the human TNF-R DNA sequence as a hybridization probe to isolated TNF-cDNAs from mammalian cDNA libraries.

Derivatives of TNF-R within the scope of the invention also include various structural forms of the primary protein which retain biological activity. Due to the presence of ionizable amino and carboxyl groups, for example, a TNF-R protein may be in the form of acidic or basic salts, or may be in neutral forms. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to TNF-R amino acid side chains or at the N- or C-termini. Other derivatives of TNF-R within the scope of this invention include covalent or aggregative conjugates of TNF-F or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its sites of synthesis to its site of function inside or outside of the cell membrane or wall (e.g., the yeast α-factor leader). TNF-R protein fusions can comprise peptides added to facilitate purification or identification of TNF-R (e.g., poly-His). The amino acid sequence of TNF receptor can also be linked to the peptide Asp-Tyr-Lys-Asp-Asp-Asp-Asp-Lys (DYKDDDDK) (Hopp et al., *Bio/Technology* 6:1204, 1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation of *E. coli*.

TNF-R derivatives may also be used as immunogens, reagents in receptor-based immunoassays, or as binding agents for affinity purification procedures of TNF or other binding ligands. TNF-R derivatives may also be obtained by cross-linking agents, such as M-maleimidobenzoyl succinimide ester and N-hydroxysuccinimide, at cysteine and lysine residues. TNF-R proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, TNF-R may be used to selectively bind (for purposes of assay or purification) anti-TNF-R antibodies or TNF.

The present invention also includes TNF-R with or without associated native-pattern glycosylation. TNF-R expressed in yeast or mammalian expression systems, e.g., COS-7 cells, may be similar or slightly different in molecular weight and glycosylation pattern than the native molecules, depending upon the expression system. Expression of TNF-R DNAs in bacteria such as *E. coli* provides non-glycosylated molecules. Functional mutant analogs of mammalian TNF-R having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

TNF-R derivatives may also be obtained by mutations of TNF-R or its subunits. A TNF-R mutant, as referred to herein, is a polypeptide homologous to TNF-R but which has an amino acid sequence different from native TNF-R because of a deletion, insertion or substitution.

Bioequivalent analogs of TNF-R proteins may be constructed by, for example, making various substitutions of residues or sequences of deleting terminal or internal residues or sequences not needed for biological activity. For example, cysteine residues can be deleted (e.g., $Cys^{178}$) or replaced with other amino acids to prevent formation of unnecessary or incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively, i.e., the most preferred substitute amino acids are those having physiochemical characteristics resembling those of the residue to be replaced. Similarly, when a deletion or insertion strategy is adopted, the potential effect of the deletion or insertion on biological activity should be considered. Substantially similar polypeptide sequences, as defined above, generally comprise a like number of amino acid sequences, although C-terminal truncations for the purpose of constructing soluble TNF-Rs will contain fewer amino acid sequences. In order to preserve the biological activity of TNF-Rs, deletions and substitutions will preferably result in homologous or conservatively substituted sequences, meaning that a given residue is replaced by a biologically similar residue. Examples of conservative substitutions include substitution of one aliphatic residue for another, such as Ile, Val, Leu, or Ala for one another, or substitutions of one polar residue for another, such as between Lys and Arg; Glu and Asp; or Gly and Asn. Other such conservative substitutions, for example, substitutions of entire regions having similar hydrophobicity characteristics, are well known. Moreover, particular amino acid differences between human, murine and other mammalian TNF-Rs is suggestive of additional conservative substitutions that may be made without altering the essential biological characteristics of TNF-R.

Subunits of TNF-R may be constructed by deleting terminal or internal residues or sequences. Particularly preferred sequences include those in which the transmembrane region and intracellular domain of TNF-R are deleted or substituted with hydrophilic residues to facilitate secretion of the receptor into the cell culture medium. The resulting protein is referred to as a soluble TNF-R molecular which retains its ability to bind TNF. A particularly preferred soluble TNF-R construct is TNF-RΔ235 (the sequence of amino acids 1–235 of FIGS. 2A–2C), which comprises the entire extracellular region of TNF-R, terminating with Asp$^{235}$ immediately adjacent the transmembrane region. Additional amino acids may be deleted from the extracellular region while retaining TNF binding activity. For example, huTNF-RΔ183 which comprises the sequence of amino acids 1–183 of FIG. 2A–2B, and TNF-RΔ163 which comprises the sequence of amino acids 1–163 of FIGS. 2A–2B, retain the ability of bind TNF ligand as determined using the binding assays described below in Example 1. TNF-RΔ142, however, does not retain the ability to bind TNF-ligand. This suggests that one or both of Cys$^{157}$ and Cys163 is required for formation of an intramolecular disulfide bridge for the proper folding of TNF-R. Cys$^{178}$, which was deleted without any apparent adverse effect on the ability of the soluble TNF-R to bind TNF, does not appear to be essential for proper folding of TNF-R. Thus, any deletion C-terminal to Cys$^{163}$ would be expected to result in a biologically active soluble TNF-R. The present invention contemplates such soluble TNF-R constructs corresponding to all or part of the extracellular region of TNF-F terminating with any amino acid after Cys$^{163}$. Other C-terminal deletions, such as TNF-RΔ157, may be made as a matter of convenience by cutting TNF-R c DNA with appropriate restriction enzymes and, if necessary, reconstructing specific sequences with synthetic oligonucleotide linkers. The resulting soluble TNF-R constructs are then inserted and expressed in appropriate expression vectors and assayed for the ability to bind TNF, as described in Example 1. Biologically active soluble TNF-Rs resulting from such constructions are also contemplated to be within the scope of the present invention.

Mutations in nucleotide sequences constructed for expression of analog TNF-R must, of course, preserve the reading frame phase of the coding sequences and preferably will not create complementary regions that could hybridize to produce secondary mRNA structures such as hoops or hairpins which would adversely affect translation of the receptor mRNA. Although a mutation site may be predetermined, it is not necessary that the nature of the mutation per se by predetermined. For example, in order to select for optimum characteristics of mutants at a given site, random mutagenesis may be conducted at the target codon and the expressed TNF-R mutants screened for the desired activity.

Not all mutations in the nucleotide sequence which encodes TNF-R will be expressed in the final product, for example, nucleotide substitutions may be made to enhance expression, primarily to avoid secondary structure loops in the transcribed mRNA (see EPA 74,444A, incorporated herein by reference), to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al., (*Gene* 37:73, 1985); Craik (*BioTechniques*, January 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Both monovalent forms and polyvalent forms of TNF-R are useful in the compositions and methods of this invention. Polyvalent forms possess multiple TNF-R binding sites for TNF ligand. For example, a bivalent soluble TNF-R may consist of two tandem repeats of amino acids 1–235 of FIGS. 2A–2C, separated by a linker region. Alternate polyvalent forms may also be constructed, for example, by chemically coupling TNF-R to any clinically acceptable carrier molecule, a polymer selected from the group consisting of Ficoll, polyethylene glycol or dextran using conventional coupling techniques. Alternatively, TNF-R may be chemically coupled to biotin, and the biotin-TNF-R conjugate then allowed to bind to avidin, resulting in tetravalent avidin/biotin/TNF-R molecules. TNF-R may also be covalently coupled to dinitrophenol (DNP) or trinitrophenol (TNP) and the resulting conjugate precipitated with anti-DNP or anti-TNP-IgM, to form decameric conjugates with a valency of 10 for TNF-R binding sites.

A recombinant chimeric antibody molecule may also be produced having TNF-R sequences substituted for the variable domains of either or both of the immunoglobulin molecule heavy and light chains and having unmodified constant region domains. For example, chimeric TNF-R/IgG$_1$ may be produced from two chimeric genes—a TNF-R/human κ light chain chimera (TNF-R/C$_κ$) and a TNF-R/human γ$_1$ heavy chain chimera (TNF-R/C$_{γ-1}$). Following transcription and translation of the two chimeric genes, the gene products assemble into a single chimeric antibody molecule having TNF-R displayed bivalently. Such polyvalent forms of TNF-R may have enhanced binding affinity for TNF ligand. Additional details relating to the construction of such chimeric antibody molecules are disclosed in WO 89/09622 and EP 315062.

Expression of Recombinant TNF-R

The present invention provides recombinant expression vectors to amplify or express DNA encoding TNF-R. Recombinant expression vectors are replicable DNA constructs which have synthetic or cDNA-derived DNA fragments encoding mammalian TNF-R or bioequivalent analogs operably linked to suitable transcriptional or translational regulatory elements derived from mammalian, microbial, viral or insect genes. A transcriptional unit generally comprises an assembly of (1) a genetic element of elements having a regulatory role in gene expression, for example, transcriptional promoters or enhancers, (2) a structural or coding sequence which is transcribed into mRNA and translated into protein, and (3) appropriate transcription and translational initiation and termination sequences, as described in detail below. Such regulatory elements may include an operator sequence to control transcription, a sequence encoding suitable mRNA ribosomal binding sites. The ability to replicate in a host, usually conferred by an origin of replication, and a selection gene to facilitate recognition of transformants may additionally be incorporated. DNA regions are operably linked when they are functionally related to each other. For example, DNA for a signal peptide (recovery leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally by subsequently cleaved from the expressed recombinant protein to provide a final product.

DNA sequences encoding mammalian TNF receptors which are to be expressed in a microorganism will preferably contain no introns that could prematurely terminate transcription of DNA into mRNA; however, premature termination of transcription may be desirable, for example, where it would result in mutants having advantageous C-terminal truncations, for example, deletion of a transmembrane region to yield a soluble receptor not bound to the cell membrane. Due to code degeneracy, there can be considerable variation in nucleotide sequences encoding the same amino acid sequence. Other embodiments include sequences capable of hybridizing to the sequences of the provided cDNA under moderately stringent conditions (50° C., 2× SSC) and other sequences hybridizing or degenerate to those which encode biologically active TNF receptor polypeptides.

Recombinant TNF-F DNA is expressed or amplified in a recombinant expression system comprising a substantially homogeneous monoculture of suitable host microorganisms, for example, bacteria such as *E. coli* or yeast such as *S. cerevisiae*, which have stably integrated (by transformation or transfection) a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence of synthetic gene to be expressed.

Transformed host cells are cell which have been transformed or transfected with TNF-R vectors constructed using recombinant DNA techniques. Transformed host cells ordinarily express TNF-R, but host cells transformed for purposes of cloning or amplifying TNF-R DNA do not need to express TNF-R. Expressed TNF-R will be deposited in the cell membrane or secreted into the culture supernatant, depending on the TNF-R DNA selected. Suitable host cells for expression of mammalian TNF-R include prokaryotes, yeast or higher eukaryotic cells under the control of appropriate promoters. Prokaryotes includes gram negative or gram positive organisms, for example *E. coli* or bacilli. Higher eukaryotic cells include established cell lines of mammalian origin as described below. Cell-free translation systems could also be employed to produce mammalian TNF-R using RNAs derived from the DNA constructs of the present invention. Appropriate cloning and expression for use with bacterial, fungal, yeast, and mammalian cellular hosts are described by Pouwels et al. (*Cloning Vectors; A Laboratory Manual*, Elsevier, N.Y., 1985), the relevant disclosure of which is hereby incorporated by reference.

Prokaryotic expression hosts may be used for expression of TNF-R that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter systems (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phase λ $P_L$ promoter and cI857ts thermolabile repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

Recombinant TNF-R proteins may also be expressed in yeast hosts, preferably from the Saccharomyces species, such as *S. cerevisiae*. Yeast of other genera, such as Pichia or Kluyveromyces may also be employed. Yeast vectors will generally contain an origin or replication from the 2μ plasmid or an autonomously replicating sequence (ARS), promoter, DNA encoding TNF-R, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* TRP1 and URA3 gene, which provides a selection marker for a mutant strain of yeast lacking the ability to grown in tryptophan, and a promoter derived from a highly expressed yeast gene to induce transcription of a structural sequence downstream. The presence of the TRP1 and URA3 lesion in the yeast host cell genome then provides an effective environment for detecting transformation by growth in the absence of tryptophan or uracil.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glutaraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pUC18 for selection and replication in *E. coli* ($Amp^r$ gene and origin of replication) and yeast DNA sequences including a glucose-repressible ADH2 promoter and α-factor secretion leader. The ADH2 promoter has been described by Russel et al. (*J. Biol. Chem.* 258:2674, 1982) and Beirer et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sties to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 μg/ml adenine and 20 μg/ml uracil or URA+ transformants in medium consisting of 0.67% YNB, with amino acids and bases as described by Sherman et al., *Laboratory Course Manual for Methods in Yeast Genetics*, Cold Spring Harbor Laboratory, Cold Spring Harbor, N.Y., 1986.

Host strains transformed by vectors comprising the ADH2 promoter may be grown for expression in a rich medium consisting of 1% yeast extract, 2% peptone, and 1% or 4% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems are also advantageously employed to express recombinant protein. Expression of recombinant proteins in mammalian cells is particularly preferred because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' and 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47(1988).

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind 3 site toward the Bgl1 site located in the viral origin of replication is included. Further, mammalian genomic TNF-R promoter, control and/or signal sequences may be utilized, provided such control sequences are compatible with the host cell chosen. Additional details regarding the use of a mammalian high expression vector to produce a recombinant mammalian TNF receptor are provided in Examples 2 and 7 below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

In preferred aspects of the present invention, recombinant expression vectors comprising TNF-R cDNAs are stably integrated into a host cell's DNA. Elevated levels of expression product is achieved by selecting for cell lines having amplified numbers of vector DNA. Cell lines having amplified numbers of vector DNA are selected, for example, by transforming a host cell with a vector comprising a DNA sequence which encodes an enzyme which is inhibited by a known drug. The vector may also comprise a DNA sequence which encodes a desired protein. Alternatively, the host cell may be co-transformed with a second vector which comprises the DNA sequence which encodes the desired protein. The transformed or co-transformed host cells are then cultured in increasing concentrations of the known drug, thereby selecting for drug-resistant cells. Such drug-resistant cells survive in increased concentrations of the toxic drug by over-production of the enzyme which is inhibited by the drug, frequently as a result of amplification of the gene encoding the enzyme. Where drug resistance is caused by an increase in the copy number of the vector DNA encoding the inhibitable enzyme, there is a concomitant co-amplification of the vector DNA encoding the desired protein (TNF-R) in the host cell's DNA.

A preferred system for such co-amplification uses the gene for dihydrofolate reductase (DHFR), which can be inhibited by the drug methotrexate (MTX). To achieve co-amplification, a host cell which lacks an active gene encoding DNFR is either transformed with a vector which comprises DNA sequence encoding DHFR and a desired protein, or is co-transformed with a vector comprising a DNA sequence encoding DNFR and a vector comprising a DNA sequence encoding the desired protein. The transformed or co-transformed host cells are cultured in media containing increasing levels of MTX, and those cell lines which survive are selected.

A particularly preferred co-amplification system uses the gene for glutamine synthetase (GS), which is responsible for the synthesis of glutamate and ammonia using the hydrolysis of ATP to ADP and phosphate to drive the reaction. GS is subject to inhibition by a variety of inhibitors, for example methionine sulphoximine (MSX). Thus, TNF-R can be expressed in high concentrations by co-amplifying cells transformed with a vector comprising the DNA sequence for GS and a desired protein, or co-transformed with a vector comprising a DNA sequence encoding GS and a vector comprising a DNA sequence encoding the desired protein, culturing the host cells in media containing increasing levels of MSX and selecting for surviving cells. The GS co-amplification system, appropriate recombinant expression vectors and cell lines, are described in the following PCT applications: WO 87/04462, WO 89/01036, WO 89/10404 and WO 86/05807.

Recombinant proteins are preferably expressed co-amplification of DHFR or GS in a mammalian host cell, such as Chinese Hamster Ovary (CHO) cells, or alternatively in a murine myeloma cell line, such as SP2/0-Ag14 or NS0 or a rat myeloma cell line, such as YB2/3.0-Ag20, disclosed in PCT applications WO/89/10404 and WO 86/05807.

A preferred eukaryotic vector for expression of TNF-R DNA is disclosed below in Example 2. This vector, referred to as pCAV/NOT, was derived from the mammalian high expression vector pDC201 and contains regulatory sequences from SV40, adenovirus-2, and human cytomegalovirus.

Purification of Recombinant TNF-R

Purified mammalian TNF receptors or analogs are prepared by culturing suitable host/vector systems to express the recombinant translation products of the DNAs of the present invention, which are then purified from culture media or cell extracts.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise a TNF or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify a TNF-R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian TNF-R can be disrupted by any convenient method, including freeze-thawing cycling, sonication, mechanical disruption, or use of cell lysing agents.

Fermentation of yeast which express mammalian TNF-R as a secreted protein greatly simplifies purification. Secreted recombinant protein resulting from a large-scale fermentation can be purified by methods analogous to those disclosed by Urdal et al., (*J. Chromatog.* 296:171, 1984). This reference describes two sequential, reversed-phase HPLC steps for purification of recombinant human GM-CSF on a preparative HPLC column.

Human TNF-R synthesized in recombinant culture is characterized by the presence of non-human cell components, including proteins, in amounts and of a character which depend upon the purification steps taken to recover human TNF-R from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of TNF-R free of proteins which may be normally associated with TNF-R as it is found in nature in its species of origin, e.g. in cells, cell exudates or body fluids.

Therapeutic Administration of Recombinant Soluble TNF-R

The present invention provides methods of using therapeutic compositions comprising an effective amount of soluble TNF-R proteins and a suitable diluent and carrier, and methods for suppressing TNF-dependent inflammatory responses in humans comprising administering an effective amount of soluble TNF-R protein.

For therapeutic use, purified soluble TNF-R protein is administered to a patient, preferably a human, for treatment in a manner appropriate to the indication. Thus, for example, soluble TNF-R protein compositions can be administered by bolus injection, continuous infusion, sustained release from implants, or other suitable techniques. Typically, a soluble TNF-R therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the TNF-R with buffers, antioxidants such as ascorbic acid, low molecular weight (less than 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

Soluble TNF-F proteins are administered for the purpose of inhibiting TNF-dependent responses. A variety of diseases or conditions are believed to be caused by TNF, such as cachexia and septic shock. In addition, other key cytokines (IL-1, IL-2 and other colony stimulating factors) can also induce significant host production of TNF. Soluble TNF-R compositions may therefore be used, for example, to treat cachexia or septic shock or to treat side effects associated with cytokine therapy. Because of the primary roles IL-1 and IL-2 play in the production of THF, combination therapy using both IL-1 receptors or IL-2 receptors may be preferred in the treatment of TNF-associated clinical indications.

The following examples are offered by way of illustration, and not by way of limitation.

EXAMPLES

Example 1

Binding Assays

A. Radiolabeling of TNFα and TNFβ. Recombinant human TNFα, in the form of a fusion protein containing a hydrophilic octapeptide at the N-terminus, was expressed in yeast as a secreted protein and purified by affinity chromatography (Hopp et al., *Bio/Technology* 6:1204, 1988). Purified recombinant human TNFβ was purchased from R&D Systems (Minneapolis, Minn.). Both proteins were radiolabeled using the commercially available solid phase agent, IODO-GEN (Pierce). In this procedure, 5 μg of IODO-GEN were plated at the bottom of a 10×75 mm glass tube and incubated for 20 minutes at 4° C. with 75 μl of 0.1 M sodium phosphate, pH 7.4 and 20 μl (2 mCi) Na $^{125}$I. This solution was then transferred to a second glass tube containing 5 μg TNFα (or TNFβ) in 45 μl PBS for 20 minutes at 4° C. The reaction mixture was fractionated by gel filtration on a 2 ml bed volume of Sephadex G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-TNF was diluted to a working stock solution of $1\times10^{-7}$ M in binding medium and stored for up to one month at 4° C. without detectable loss of receptor binding activity. The specific activity is routinely $1\times10^6$ cpm/mmole TNF.

B. Binding to Intact Cells. Binding assays with intact cells were performed by two methods. In the first method, cells were first grown either in suspension (e.g., U 937) or by adherence on tissue culture plates (e.g., WI26-VA4, COS cells expressing the recombinant TNF receptor). Adherent cells were subsequently removed by treatment with 5 mM EDTA treatment for ten minutes at 37 degrees centrigrade. Binding assays were then performed by a pthalate oil separation method (Dower et al., *J. Immunol.* 132:751, 1984) essentially as described by Park et al. (*J. Biol. Chem.* 261:4177, 1986). Non-specific binding of $^{125}$I-TNF was measured in the presence of a 200-fold or greater molar excess of unlabeled TNF. Sodium azide (0.2%) was included in a binding assay to inhibit internalization of $^{125}$I-TNF by cells. In the second method, COS cells transfected with the TNF-R-containing plasmid, and expressing TNF receptors on the surface, were tested for the ability to bind $^{125}$I-TNF by the plate binding assay described by Sims et al. (*Science* 241:585, 1988).

C. Solid Phase Binding Assays. The ability of TNF-R to be stably adsorbed to nitrocellulose from detergent extracts of human cells yet retain TNF-binding activity provided a means of detecting TNF-R. Cell extracts were prepared by mixing a cell pellet with a 2×volume of PBS containing 1% Triton X-100 and a cocktail of protease inhibitors (2 mM phenylmethylsulfonyl fluoride, 10 μM pepstatin, 10 μM leupeptin, 2 mM o-phenanthroline and 2 mM EGTA) by vigorous vortexing. The mixture was incubated on ice for 30 minutes after which it was centrifuged at 12,000×g for 15 minutes at 8° C. to remove nuclei and other debris. Two microliter aliquots of cell extracts were placed on dry BS85/21 nitrocellulose membranes (Schleicher and Schuell, Keene, N.H.) and allowed to dry. The membranes were incubated in tissue culture dishes for 30 minutes in Tris (0.05 M) buffered saline (0.15 M) pH 7.5 containing 3% w/v BSA to block nonspecific binding sites. The membrane was then covered with $5\times10^{-11}$ M $^{125}$I-TNF in PBS+3% BSA and incubated for 2 hr at 4° C. with shaking. At the end of this time, the membranes were washed 3 times in PBS, dried and placed on Kodak X-Omat AR film for 18 hr at –70° C.

Example 2

Isolation of Human TNF-R cDNA by Direct Expression of Active Protein in COS-7 cells Various human cell lines were screened for expression of TNF-R based on their ability to bind $^{125}$I-labeled TNF. The human fibroblast cell line WI-26 VA4 was found to express a reasonable number of receptors per cell. Equilibrium binding studies showed that the cell line exhibited biphasic binding of $^{125}$I-TNF with approximately 4,000 high affinity sites ($K_a=1\times10^{10}$ M$^{-1}$) and 15,000 low affinity sites ($K_a=1\times10^8$ M$^{-1}$) per cell.

An unsized cDNA library was constructed by reverse transcription of polyadenylated mRNA isolated from total RNA extracted from human fibroblast WI-26 VA4 cells grown in the presence of pokeweed mitogen using standard techniques (Gubler, et al., *Gene* 25:263, 1983; Ausubel et al., eds., *Current Protocols in Molecular Biology*, Vol. 1, 1987). The cells were harvested by lysing the cells in a guanidine hydrochloride solution and total RNA isolated as previously described (March et al., *Nature* 315:641, 1985).

Poly A$^+$ RNA was isolated by oligo dT cellulose chromatography and double-stranded cDNA was prepared by a method similar to that of Gubler and Hoffman (*Gene* 25:263, 1983). Briefly, the poly A$^+$ RNA was converted to an RNA-cDNa hybrid by reverse transcriptase using oligo dT as a primer. The RNA-cDNA hybrid was then converted into double-stranded cDNA using RNAase H in combination with DNA polymerase I. The resulting double stranded cDNA was blunt-ended with T4 DNA polymerase. To the blunt-ended cDNA is added EcoRI linker-adapters (having internal Not1 sites) which were phosphorylated on only one end (Invitrogen). The linker-adapted cDNA was treated with T4 polynucleotide kinase to phosphorylate the 5' overhanging region of the linker-adapter and unligated linkers were removed by running the cDNA over a Sepharose CL4B column. The linker-adaptered cDNA was ligated to an equimolar concentration of EcoR1 cut and dephosphorylated arms of bacteriophage λgt10 (Huynh et al, *DNA Cloning: A Practical Approach*, Glover, ed., IRL Press, pp. 49–78). The ligated DNA was packaged into phage particles using a commercially available kit to generate a library of recombinants (Stratagene Cloning Systems, San Diego, Calif., USA). Recombinants were further amplified by plating phage on a bacterial lawn of *E. coli* strain c600(hfl$^-$).

Phage DNA was purified from the resulting λgt10 cDNA library and the cDNA inserts excised by digestion with the restriction enzyme Not1. Following electrophoresis of the digest through an agarose gel, cDNAs greater than 2,000 bp were isolated.

The resulting cDNAs were ligated into the eukaryotic expression vector pCAV/NOT, which was designated to express cDNA sequences inserted at its multiple cloning site when transfected into mammalian cells. pCAV/NOT was assembled from pDC201 (a derivative of pMLSV, previously described by Cosman et al., *Nature* 312: 768, 1984), SV40 and cytomegalovirus DNA and comprises, in sequence with the direction of transcription from the origin of replication: (1) SV40sequences from coordinates 5171-270 including the origin of replication, enhancer sequences and early and late promoters; (2) cytomegalovirus sequences including the promoter and enhancer regions (nucleotides 671 to +63 from the sequence published by Boechart et al. (*Cell* 41:521, 1985); (3) adenovirus-2 sequences containing the first exon and part of the intron between the first and second exons of the tripartite leader, the second exon and part of the third exon of the tripartite leader and a multiple cloning site (MCS) containing sites for Xho1, Kpn1, Sma1, Not1 and Blg1; (4) SV40 sequences from coordinates 4127-

4100 and 2770-2533 that include the polyadenylation and termination signals for early transcription; (5) sequences derived from pBR322 and virus-associated sequences VAI and VAII of PDC201, with adenovirus sequences 10532-11156 containing the VAI and VAII genes, followed by pBR322 sequences from 4363-2486 and 1094-375 containing the ampicillin resistance gene and origin of replication.

The resulting WI-26 VA4 cDNA library in pCAV/NOT was used to transform *E. coli* strain DH5α, and recombinants were plated to provide approximately 800 colonies per plate and sufficient plates to provide approximately 50,000 total colonies per screen. Colonies were scraped from each plate, pooled, and plasmid DNA prepared from each pool. The pooled DNA was then used to transfected a subconfluent layer of monkey COS-7 cells using DEAE-dextran followed by chloroquine treatment, as described by Luthman et al. (*Nucl. Acids Res.* 11:1295, 1983) and McCutchan et al. (*J. Natl. Cancer Inst.* 41:351, 1986). The cells were then grown in culture for three days to permit transient expression of the inserted sequences. After three days, cell culture supernatants were discarded and the cell monolayers in each plate assayed for TNF binding as follows. Three ml of binding medium containing $1.2 \times 10^{-11}$ M $^{125}$I-labeled FLAG®-TNF was added to each plate and the plates incubated at 4° C. for 120 minutes. This medium was then discarded, and each plate was washed once with cold binding medium (containing no labeled TNF) and twice with cold PBS. The edges of each plate were then broken off, leaving a flat disk which was contacted with X-ray film for 72 hours at −70° C. using an intensifying screen. TNF binding activity was visualized on the exposed films as a dark focus against a relatively uniform background.

After approximately 240,000 recombinants from the library had been screened in this manner, one transfectant pool was observed to provide TNF binding foci which were clearly apparent against the background exposure.

A frozen stock of bacteria from the positive pool was then used to obtain plates of approximately 150 colonies. Replicas of these plates were made on nitrocellulose filters, and the plates were then scraped and plasmid DNA prepared and transfected as described above to identify a positive plate. Bacteria form individual colonies from the nitrocellulose replica of this plate were grown in 0.2 ml cultures, which were used to obtain plasmid DNA, which was transfected into COS-7 cells as described above. In this manner, a single clone, clone 1, was isolated which was capable of inducing expression of human TNF-R in COS cells. The expression vector pCAV/NOT containing the NTF-R cDNA clone 1 has been deposited with the American Type Culture Collection, 12301 Parklawn Drive, Rockville, Md. 20852, USA (Accession No. 68088) under the name pCAV/NOT-TNF-R.

Example 3

Construction of cDNAs Encoding Soluble huTNF-RΔ235

A cDNA encoding a soluble huTNF-RΔ235 (having the sequence of amino acids 1–235 of FIGS. 2A–2C) was constructed by excising an 840 bp fragment from pCAV/NOT-TNF-R with the restriction enzymes Not1 and Pvu2. Not1 cuts at the multiple cloning site of pCAV/NOT-TNF-R and Pvu2 cuts within with TNF-R coding region 20 nucleotides 5' of the transmembrane region. In order to reconstruct the 3' end of the TNF-R sequence, two oligonucleotides were synthesized and annealed to create the following oligonucleotides linker.

```
     Pvu2                       BamH1  Egl2
     CTGAAGGGAGCACTGGCGACTAAGGATCCA
     GACTTCCCTCGTGACCGCTGATTCCTAGGTCTAG
     AlaGluGlySerThrGlyAspEnd
```

This oligonucleotide linker has terminal Pvu2 and Bgl2 restriction sites, regenerates 20 nucleotides of the TNF-R, followed by a termination codon (underlined) and a BamH1 restriction site (for convenience in isolating the entire soluble TNF-R by Not1/BamH1 digestion). This oligonucleotide was then ligated with the 840 bp Not1/Pvu2 TNF-R insert into Bgl2/Not1 cut pCAV/NOT to yield psolhuTNF-RΔ235/CAVNOT, which was transfected into COS-7 cells as described above. This expression vector induced expression of soluble human TNF-R which was capable of binding TNF.

Example 4

Construction of cDNAs Encoding Soluble huTNF-RΔ185

A cDNA encoding a soluble huTNF-RΔ185 (having the sequence of amino acids 1–185 of FIGS. 2A–2B) was constructed by excising a 640 bp fragment from pCAV/NOT-TNF-R with the restriction enzymes Not1 and Bgl2. Not1 cuts at the multiple cloning sites of pCAV/NO-TNF-R and Bgl2 cuts within the TNF-R coding region at nucleotide 637, which is 237 nucleotides 5' of the transmembrane region. The following oligonucleotide linkers were synthesized:

```
   Bgl2
5'-GATCTGTAACGTGGTGGCCATCCCTGGGAATGCAAGCATGGATGC-3'
       ACATTGCACCACCGGTAGGGACCCTTACGTTCG
       IleCysAsnValValAlaIleProGlyAsnAlaSerMetAspAla

Not1
5'-        AGTCTGCACGTCCACGTCCCCCACCCGGTGAGC   -3'
   TACCTACGTCAGACGTGCAGGTGCAGGGGGTGGGCCACTCGCCGG
              ValCysThrSerThrSerProThrArgEnd
```

The above oligonucleotide linkers reconstruct the 3' end of the receptor molecule up to nucleotide 708, followed by a termination codon (underlined). These oligonucleotides were then ligated with the 640 bp Not1 TNF-R insert into Not1 cut pCAV/NOT to yield the expression vector psolTNFRΔ185/CAVNOT, which was transfected into COS-7 cells as described above. This expression vector induced expression of soluble human TNF-R which was capable of binding TNF.

Example 5

Construction of cDNAs Encoding Soluble huTNF-RΔ163

A cDNA encoding a soluble huTNF-RΔ163 (having the sequence of amino acids 1–163 of FIGS. 2A–2B) was constructed by excising a 640 bp fragment from pCAV/NOT-TNF-R with the restriction enzymes Not1 and Bgl2 as described in Example 4. The following oligonucleotide linkers were synthesized:

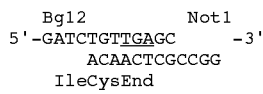
```
     Bgl2         Not1
5'-GATCTGTTGAGC       -3'
        ACAACTCGCCGG
        IleCysEnd
```

This above oligonucleotide linker reconstructs the 3' end of the receptor molecule up to nucleotide 642 (amino acid 163), followed by a termination codon (underlined). This oligonucleotide was then ligated with the 640 bp Not1 TNF-R insert into Not1 cut pCAV/NOT to yield the expression vector psolTNFRΔ163/CAVNOT, which was transfected into COS-7 cells as described above. This expression vector induced expression of soluble human TNF-R which was capable of binding TNF in the binding assay described in Example 1.

Example 6

Construction of cDNAs Encoding Soluble huTNF-RΔ142

A cDNA encoding a soluble huTNF-RΔ142 (having the sequence of amino acids 1–142 of FIGS. 2A–2B) was constructed by excising a 550 bp fragment from pCAV/NOT-TNF-R with the restriction enzymes Not1 and AlwN1. AlwN1 cuts within the TNF-R coding region at nucleotide 549. The following nucleotide linker was synthesized:

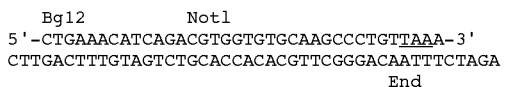
```
    Bgl2          Not1
5'-CTGAAACATCAGACGTGGTGTGCAAGCCCTGTTAAA-3'
   CTTGACTTTGTAGTCTGCACCACACGTTCGGGACAATTTCTAGA
                                              End
```

This above oligonucleotide linker reconstructs the 3' end of the receptor molecule up to nucleotide 579 (amino acid 142), followed by a termination codon (underlined). This oligonucleotide was then ligated with the 550 bp Not1/AlwN1 TNF-R insert into Not1/Bgl2 cut pCAV/NOT to yield the expression vector psolTNFRΔ142/CAVNOT, which was transfected into COS-7 cells as described above. This expression vector did not induced expression of soluble human TNF-R which was capable of binding TNF. It is believed that this particular construct failed to express biologically active TNF-R because one or more essential cysteine residue (e.g., $Cys^{157}$ or $Cys^{163}$) required for intramolecular bonding (for formation of the proper tertiary structure of the TNF-R molecule) was eliminated.

Example 7

Expression of Soluble TNF Receptors in CHO Cells

Soluble TNF receptor was expressed in Chinese Hamster Ovary (CHO) cells using the glutamine-synthetase (GS) gene amplification system, substantially as described in PCT patent application Nos. WO87/04462 and WO89/01036. Briefly, CHO cells are transfected with an expression vector containing genes for both TNF-R and GS. CHO cells are selected for GS gene expression based on the ability of the transfected DNA to confer resistance to low levels of methionine sulphoximine (MSX). GS sequence amplification events in such cells are selected using elevated MSX concentrations. In this way, contiguous TNF-R sequences are also amplified and enhanced TNF-R expression is achieved.

The vector used in the GS expression system was psolTNFR/P6/PSVLGS, which was constructed as follows. First, the vector pSVLGS.1 (described in PCT Application Nos. WO87/04462 and WO89/01036, and available from Celltech, Ltd., Berkshire, UK) was cut with the BamH1 restriction enzyme and dephosphorylated with calf intestinal alkaline phosphatase (CIAP) to prevent the vector from religating to itself. The BamH1 cut pSVLGS.1 fragment was then ligated to a 2.4 kb BamH1 to Bgl2 fragment of pEE6hCMV (described in PCT Application No. WO89/01036, also available from Celltech) which was cut with Bgl2, BamH1 and Fsp1 to avoid two fragments of similar size, to yield an 11.2 kb vector designated p6/PSVLGS.1. pSVLGS.1 contains the glutamine synthetase selectable marker gene under control of the SV40 later promoter. The BamH1 to Bgl2 fragment of pEE6hCMV contains the human cytomegalovirus major immediate early promoter (hCMV), a polylinker, and the SV40 early polyadenylation signal. The coding sequences for soluble TNF-R were added to p6/PSVLGS.1 by excising a Not1 to BamH1 fragment from the expression vector psolTNFR/CAVNOT (made according to Example 3 above), blunt ending with Klenow and ligating with SmaI cut dephosphorylated p6/PSVLGS.1, thereby placing the solTNF-R coding sequences under the control of the hCMV promoter. This resulted in a single plasmid vector in which the SV40/GS and hCMB/solTNF-R transcription units are transcribed in opposite directions. This vector was designated psolTNFR/P6/PSVLGS.

psolTNFR/P6/PSVLGS was used to transfect CHO-K1 cells (available from ATCC, Rockville, Md., under accession number CCL 61) as follows. A monolayer of CHO-K1 cells were grown to subconfluency in Minimum Essential Medium (MEM) 10X (Gibco: 330-1581AJ) without glutamine and supplemented withi 10% dialysed fetal bovine serum (Gibco: 220-6300AJ), 1 mM sodium pyruvate (Sigma), MEM non-essential amino acids (Gibco: 320-1140AG), 500 μM asparagine and glutamine (Sigma) and nucleotides (30 μM adenosine, guanosine, cytidine and uridine and 10 μM thymidine)(Sigma).

Approximately $1 \times 10^6$ cells per 10 cm petri disk were transfected with 10 ug of psolTNFR/P6/PSVLGS by standard calcium phosphate precipitation, substantially as described by Graham & van der Eb, Virology 52:456 (19893). Cells were subjected to glycerol shock (15% glycerol in serum-free culture medium for approximately 1.5 minutes) approximately 4 hours after transfection, substantially as described by Frost & Williams, Virology 91:39 (1978), and then washed with serum-free medium. One day later, transfected cells were fed with fresh selective medium containing MSV at a final concentration of 25 uM. Colonies of MSX-resistant surviving cells were visible within 3–4 weeks. Surviving colonies were transferred to 24-well plates and allowed to grow to confluency in selective medium. Conditioned medium from confluent wells were then assayed for soluble TNF-R activity using the binding assay described in Example 1 above. These assays indicated that the colonies expressed biologically active soluble TNF-R.

In order to select for GS gene amplification, several MSX-resistant cell lines are transfected with psolTNFR/P6/PSVLGS and grown in various concentrations of MSX. For each cell line, approximately $1\times10^6$ cells are plated in gradually increasing concentrations of 100 uM, 250 uM, 500 mM and 1 mM MSX and incubated for 10–14 days. After 12 days, colonies resistant to the higher levels of MSX appear. The surviving colonies are assayed for TNF-R activity using the binding assay described above in Example 1. Each of these highly resistant cell lines contains cells which arise from multiple independent amplification events. From these cell lines, one or more of the mostly highly resistant cell lines are isolated. The amplified cells with high production rates are then cloned by limiting dilution cloning. Mass cell cultures of the transfectants secrete active soluble TNF-R.

Example 8

Expression of Soluble Human TNF-R in Yeast

Soluble human TNF-R was expressed in yeast with the expression vector pIXY423, which was derived from the yeast expression vector pIXY120 and plasmid pYEP352. pIXY120 is identical to pYαHuGM (ATCC 53157), except that it contains no cDNA insert and includes a polylinker/multiple cloning site with a Nco1 restriction site.

A DNA fragment encoding TNF receptor and suitable for cloning into the yeast expression vector pIXY120 was first generated by polymerase chain reaction (PCR) amplification of the extracellular portion of the full length receptor from pCAV/NOT-TNF-R (ATCC 68088). The following primers were used in this PCR amplification:

```
5' End Primer
5'-TTCCGGTACCTTTGGATAAAAGAGACTACAAGGAC
    Asp718->ProLeuAspLysArgAspTyrLysAsp
       GACGATGACAAGTTGCCCGCCCAGGTGGCATTTACA-3'
       AspAspAspLys<--------TNF-R---------->

3' End Primer (antisense)
5'-CCCGGGATCCTTAGTCGCCAGTGCTCCCTTCAGCTGGG-3'
       BamH1>End<-------------TNF-R------>
```

The 5' end oligonucleotide primer used in the amplification included an Asp718 restriction site at its 5' end, followed by nucleotides encoding the 3' end of the yeast α-factor leader sequence (Pro-Leu-Asp-Lys-Arg) and those encoding the 8 amino acids of the FLAG® peptide (AspTyrLysAspAspAspAspLys) fused to sequence encoding the 5' end of the mature receptor. The FLAG® peptide (Hopp et al., Bio/Technology 6:1204, 1988) is a highly antigenic sequence which reversibly binds the monoclonal antibody M1 (ATCC HB 9259). The oligonucleotide used to generate the 3' end of the PCR-derived fragment is the antisense strand of DNA encoding sequences which terminate the open reading frame of the receptor after nucleotide 704 of the mature coding region (following the Asp residue preceding the transmembrane domain) by introducing a TAA stop codon (underlined). The stop codon is then followed by a BamH1 restriction site. The DNA sequences encoding TNF-R are then amplified by PCR, substantially as described by Innis et al., eds., PCR Protocols: A Guide to Methods and Applications (Academic Press, 1990).

The PCR-derived DNA fragment encoding a soluble human TNF-R was subcloned into the yeast expression vector pIXY120 by digesting the PCR-derived DNA fragment with BamH1 and Asp718 restriction enzymes, digesting pIXY120 with BamH1 and Asp718, and ligating the PCR fragment into the cut vector in vitro with T4 DNA ligase. The resulting construction (pIXY424) fused the open reading frame of the FLAG®-soluble TNF receptor in-frame to the complete α-factor leader sequence and placed expression in yeast under the aegis of the regulated yeast alcohol dehydrogenase (ADH2) promoter. Identity of the nucleotide sequence of the soluble TNF receptor carried in pIXY424 with those in cDNA clone 1 were verified by DNA sequencing using the dideoxynucleotide chain termination method. pIXY424 was then transformed into E. coli strain RR1.

Soluble human TNF receptor was also expressed and secreted in yeast in a second vector. This second vector was generated by recovering the pIXY424 plasmid from E. coli and digesting with EcoR1 and BamH1 restriction enzymes to isolate the fragment spanning the region encoding the ADH2 promoter, the α-factor leader, the FLAG®-soluble TNF receptor and the stop codon. This fragment was ligated in vitro into EcoR1 and BamH1 cut plasmid pYEP352 (Hill et al., Yeast 2:163 (1986)), to yield the expression plasmid pIXY432, which was transformed into E. coli strain RR1.

To assess secretion of the soluble human TNF receptor from yeast, pIXY424 was purified and introduced into a diploid yeast strain of S. cerevisiae (XV2181) by electroporation and selection for acquisition of the plasmid-borne yeast TRP1+ gene on media lacking tryptophan. To assess secretion of the receptor directed by pIXY432, the plasmid was introduced into the yeast strain PB149-6b by electroporation followed by selection for the plasmid-borne URA3+ gene with growth on media lacking uracil. Overnight cultures were grown at 30° C. in the appropriate selective media. The PB148-6b/pIXY434 transformants were diluted into YEP-1% glucose media and grown at 30° C. for 38–40 hours. Supernatants were prepared by removal of cells by centrifugation, and filtration of supernatants through 0.45µ filters.

The level of secreted receptor in the supernatants was determined by immuno-dotblot. Briefly, 1 ul of supernatants, and dilutions of the supernatants, were spotted onto nitrocellulose filters and allowed to dry. After blocking non-specific protein binding with a 3% BSA solution, the filters were incubated with diluted M1 anti-FLAG® antibody, excess antibody was removed by washing the then dilutions of horseradish peroxidase conjugated anti-mouse IgG antibodies were incubated withi the filters. After removal of excess secondary antibodies, peroxidase substrates were added and color development was allowed to proceed for approximately 10 minutes prior to removal of the substrate solution.

The anti-FLAG® reactive material found in the supernatants demonstrated that significant levels of receptor were secreted by both expression systems. Comparisons demonstrated that the pIXY432 system secreted approximately 8–16 times more soluble human TNF receptor than the pIXY424 system. The supernatants were assayed for soluble TNF-R activity, as described in Example 1, by their ability to bind $^{125}$I-TNFα and block TNFα binding. The pISY432 supernatants were found to contain significant levels of active soluble TNF-R.

Example 9

Isolation of Murine TNF-R cDNAs

Murine TNF-R cDNAs were isolated from a cDNA library made from murine 7B9 cells, an antigen-dependent helper T cell line derived from C57BL/6 mice, by cross-species hybridization with a human TNF-R probe. The cDNA library was constructed in λZAP (Stratagene, San Diego), substantially as described above in Example 2, by isolating polyadenylated RNA from the 7B9 cells.

A double-stranded human TNF-R cDNA probe was produced by excising an approximately 3.5 kb Not1 fragment of the human TFN-R clone 1 and $^{32}$P-labeling the cDNA using random primers (Boehringer-Mannheim).

The murine cDNA library was amplified once and a total of 900,000 plaques were screened, substantially as described in Example 2, with the human TNF-R cDNA probe. Approximately 21 positive plaques were identified, and the Bluescript plamids containing EcoR1-linkered inserts were excised (Stratagene, San Diego). Nucleic acid sequencing of a portion of murine TNF-R clone 11 indicated that the coding sequence of the murine TNF-R was approximately 88% homologous to the corresponding nucleotide sequence of human TNF-R. A partial nucleotide sequence of murine TNF-R cDNA clone 11 is set forth in FIGS. 3A–3D.

Example 10

Preparation of Monoclonal Antibodies to TNF-R

Preparations of purified recombinant TNF-R, for example, human TNF-R, or transfected COS cells expressing high levels of TNF-R are employed to generate monoclonal antibodies against TNF-R using conventional techniques, for example, those disclosed in U.S. Pat. No. 4,411,993. Such antibodies are likely to be useful in interfering with TNF binding to TNF receptors, for example, in ameliorating toxic or other undesired effects of TNF, or as components of diagnostic or research assays for TNF of soluble TNF receptor.

To immunize mice, TNF-R immunogen is emulsified in complete Freund's adjuvant and injected in amounts ranging from 10–100 μg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with TNF-R, for example, by adaptations of the techniques disclosed by Engvall et al., *Immunochem.* 8:871 (1971) and in U.S. Pat. No. 4,703,004. Positive clones are then injected into the peritoneal cavities of syngeneic Balb/c mice to produce ascites containing high concentrations (>1 mg/ml) of anti-TNF-R monoclonal antibody. The resulting monoclonal antibody can be purified by ammonium sulfate precipitation followed by gel exclusion chromatography, and/or affinity chromatography based on binding of antibody to Protein A of *Staphylococcus aureas.*

We claim:

1. A recombinant protein comprising amino acids 1–163 of FIGS. 2A–2B, and wherein said recombinant protein binds TNF.

2. The recombinant protein of claim 1, wherein said protein comprises amino acids 1–185 of FIGS. 2A–2B.

3. The recombinant protein of claim 1, wherein said protein comprises amino acids 1–235 of FIGS. 2A–2C.

4. The recombinant protein of claim 1, wherein said extracellular region does not have native-pattern glycosylation.

* * * * *